United States Patent
Siebeneicher et al.

(10) Patent No.: US 8,968,701 B2
(45) Date of Patent: Mar. 3, 2015

(54) USAGE OF LOW TO MEDIUM-PRESSURE LIQUID CHROMATOGRAPHY FOR THE PURIFICATION OF RADIOTRACERS

(75) Inventors: Holger Siebeneicher, Berlin (DE); Keith Graham, Berlin (DE); Mathias Berndt, Berlin (DE)

(73) Assignee: Piramal Imaging SA, Matran (CH)

( * ) Notice: Subject to any disclaimer, the term of this patent is extended or adjusted under 35 U.S.C. 154(b) by 251 days.

(21) Appl. No.: 13/383,224

(22) PCT Filed: Jul. 6, 2010

(86) PCT No.: PCT/EP2010/004112
§ 371 (c)(1),
(2), (4) Date: Mar. 29, 2012

(87) PCT Pub. No.: WO2011/003591
PCT Pub. Date: Jan. 13, 2011

(65) Prior Publication Data
US 2012/0184749 A1 Jul. 19, 2012

(30) Foreign Application Priority Data

Jul. 10, 2009 (EP) .................................... 09009009
Jan. 14, 2010 (EP) .................................... 10075022

(51) Int. Cl.
*A61K 51/00* (2006.01)
*A61M 36/14* (2006.01)
*C07B 59/00* (2006.01)

(52) U.S. Cl.
CPC ...................................... *C07B 59/00* (2013.01)
USPC ........... 424/1.89; 546/300; 422/547; 564/414

(58) Field of Classification Search
None
See application file for complete search history.

(56) References Cited

U.S. PATENT DOCUMENTS

| 7,807,135 | B2 | 10/2010 | Kung et al. |
| 7,847,092 | B2 | 12/2010 | Moon et al. |
| 2008/0305042 | A1 | 12/2008 | Gacek et al. |

FOREIGN PATENT DOCUMENTS

| CA | 101336114 | | 12/2008 |
| CN | 101094824 | A | 12/2007 |
| CN | 101123995 | A | 2/2008 |
| JP | 2008-524243 | A | 7/2008 |
| JP | 2009-518371 | A | 5/2009 |
| JP | 2010-525931 | A | 7/2010 |
| WO | 2006/066104 | A2 | 6/2006 |
| WO | 2007002540 | A2 | 1/2007 |
| WO | 2007/066089 | A2 | 6/2007 |
| WO | 2008/110757 | A1 | 9/2008 |

OTHER PUBLICATIONS

Marston et al. Natural Product Reports, 1991, 391-413.*
Tuong et al. Analytical Biochem. 189, 186-191 (1990).*
Chinese Office Action dated Jul. 31, 2013 issued in corresponding Application No. 201080031248.4 (pp. 1-6).
English language translation of the text of the Office Action dated Jul. 31, 2013 issued in corresponding Application No. 201080031248.4 (pp. 1-6).
Search Report dated Jul. 23, 2013 issued in corresponding Chinese Application No. 201080031248.4 (pp. 1-2).
English language translation of the text of the Search Report dated Jul. 23, 2013 issued in corresponding Application No. 201080031248.4 (pp. 1-2).
Office Action issued in corresponding EP Application No. 10 734 910.2. Dated: May 7, 2014. (3 pages).
CN Office Action in parallel Chinese Patent Application No. 201080031248.4 issued Jan. 24, 2014.
English Translation of CN Office Action in parallel Chinese Patent Application No. 201080031248.4 issued Jan. 24, 2014.
JP Office Action in parallel Japanese Patent Application No. 2012-518815 issued Mar. 26, 2014.

* cited by examiner

*Primary Examiner* — Maria Leavitt
*Assistant Examiner* — Sean R Donohue
(74) *Attorney, Agent, or Firm* — Millen, White, Zelano & Branigan, P.C.

(57) ABSTRACT

The invention relates to a process for the production of radiotracers. In particular, this invention relates the isolation of radiotracers with containers filled with a stationary phase.

9 Claims, 10 Drawing Sheets

USAGE OF LOW TO MEDIUM-PRESSURE LIQUID CHROMATOGRAPHY FOR THE PURIFICATION OF RADIOTRACERS

FIELD OF INVENTION

The invention relates to a process for the production of radiotracers. In particular, this invention relates the isolation of radiotracers with containers filled with a stationary phase.

BACKGROUND

In the preparation of radiopharmaceuticals strategies to remove by-products, such as excess precursors have to be established for successful (radio-) synthesis and subsequent safe administration of compounds of clinical interest. Such reactions often employ non-radioactive organic precursors in amounts that are in large excess relative to the amount of the radiolabeling agent used. Excess precursors must then be removed from the reaction mixture before the radiolabeled compound can be applied to a patient for diagnostic and/or therapeutic applications.

Strategies to remove by-products, such as excess precursors have to be established for successful (radio-) synthesis and subsequent safe administration of compounds of clinical interest. Such reactions often employ non-radioactive organic precursors in amounts that are in large excess relative to the amount of the radiolabeling agent used. Excess precursors must then be removed from the reaction mixture before the radiolabeled compound can be applied to a patient for diagnostic and/or therapeutic applications.

The purification of the radiolabeled compound is normally achieved via a solid phase extraction (SPE) or a high-pressure liquid-chromatography (HPLC). Considering the half-life of most clinically useful radioisotopes, it is desirable to complete the radiosynthesis and purification prior to administration to a patient as rapidly as possible. For example, the half-life of 18 F is 110 minutes and 18 F-labeled targeting substrates are therefore synthesized and purified within one hour of clinical use. Regarding these time restrictions an HPLC purification is often time-consuming and tedious. Moreover this technique requires specialized equipment and can not be part of a disposable synthesis kit for cassette-type modules. This demands a purification and equilibrium of the HPLC prior the next synthesis. However, the same condition of the HPLC, especially of the HPLC column can not be guaranteed for every production run. Consequently, the consistency of the process can not be ensured.

With regard to technical requests and time-consumption a SPE purification is much less demanding and the SPE cartridges can also be part of a disposable synthesis kit for cassette-type modules. Nevertheless the cartridges used for purification of the radiolabeled compounds normally contain solid phase material in the range from 20 mg to 2 g. With this amount the complete removal of all by-products is often tedious and in many cases even not achievable. In view of the above, it is readily apparent that there is a need in the art for purification strategies which offer a reproducible, rapid and efficient separation of unwanted species from the final radiolabeled compound.

The current invention solves this technical problem by applying a disposable container for purification instead of using a multi-run HPLC purification step.

SUMMARY OF THE INVENTION

The present invention generally relates the use of a normal or reversed-phase flash chromatography to purify radiolabeled compounds from any kind of by-products.

This flash chromatography is performed by any kind of disposable container filled with the solid phase material. These containers can be connected to any kind of flush system via tubings and can therefore be part of a disposable synthesis kit for radiopharmaceuticals on a cassette-type module or belong to a non-cassette-type module.

DESCRIPTION OF THE INVENTION

In the first aspect, the present invention relates to processes for the production of radiopharmaceuticals comprising the steps of:
radiolabeling of a precursor molecule and,
purification of the radiolabeled tracer from excess of precursor and by-products using a container.

Optionally, further chemical transformations can be part of the process.

The purification of the radiotracer comprises the step of liquid chromatography, wherein this liquid chromatography is a low- to medium-pressure liquid chromatography. In a preferred embodiment, the pressure of the low to medium-pressure liquid chromatography is between 1 and 20 bar, more preferable between 1 and 10 bar, even more preferably between 1 and 5 bar.

The radiolabeled compound contains at least one radioisotope that is selected in the group $^{99m}Tc$, $^{111}In$, $^{18}F$, $^{201}Tl$, $^{123}I$, $^{124}I$, $^{125}I$, $^{131}I$, $^{34}Cl$, $^{11}C$, $^{32}P$, $^{72}As$, $^{76}Br$, $^{89}Sr$, $^{153}Sm$, $^{186}Re$, $^{188}Re$, $^{212}Bi$, $^{213}Bi$, $^{89}Zr$, $^{86}Y$, $^{90}Y$, $^{67}Cu$, $^{64}Cu$, $^{192}Ir$, $^{165}Dy$, $^{177}Lu$, $^{117m}Sn$, $^{213}Bi$, $^{212}Bi$, $^{211}At$, $^{225}Ac$, $^{223}Ra$, $^{169}Yb$, $^{68}Ga$ and $^{67}Ga$.

In a preferred embodiment, the radiolabeled tracer is bearing a radioactive isotope for positron-emission-tomography.

In a more preferred embodiment, the radioisotope is selected from the group comprising $^{18}F$, $^{68}Ga$.

The radiotracer can be used for imaging of CNS, cardiovascular or oncological diseases.

In a preferred embodiment, the radiolabeled tracer is used for imaging of CNS disorders, preferable for detecting of Aβ plaques. Such tracers comprise aryl(or hetaryl)vinyl aniline derivatives such as, but not limited to 4-[(E)-2-(4-{2-[2-(2-[F-18]fluoroethoxy)ethoxy]ethoxy}-phenyl)vinyl]-N-methylaniline, 4-[(E)-2-(6-{2-[2-(2-[F-18]fluoroethoxy)ethoxy]ethoxy}pyridin-3-yl)vinyl]-N-methylaniline.

The container is a cartridge, column or any kind of cylinder.

The container is made from any kind of metal, alloy, plastic, glass, carbon or mixtures thereof.

In a preferred embodiment the material for the container is selected from the group of any kind of plastic, glass or mixture thereof, more preferably selected from USP class VI plastics, and even more preferably from medical-grade polyethylene or polypropylene.

The container is filled with a stationary phase.

The container can contain additional parts such as but not limited to: porous frits, connectors and adaptors.

In a preferred embodiment, the stationary phase is selected from the group comprising silica gel, modified silica gel, alumina, resins, polymers, copolymers or mixtures or layers thereof.

In a more preferred embodiment, the stationary phase is selected from the group comprising silica, alumina A, alumina B, alumina N, magnesium silicate, magnesium oxide, zirconium oxide, C30, C18, tC18, C8, C4, C2, tC2, amino propyl (NH2), cyano propyl (CN), diol, hydroxyapatite, cellulose, graphitized carbon and polystyrene/divinylbenzene polymers or copolymers thereof.

10 µg to 100 g of the stationary phase are filled into the container. In a preferred embodiment, 100 mg to 50 g of the stationary phase are filled into the container. In a more preferred embodiment 2 g to 20 g of the stationary phase are filled into the container. Even more preferably, 3.5 g to 10 g of the stationary phase are filled into the container.

One or more of the containers of same or different dimension filled with the same or different stationary phases can be used for the process.

The container filled with the stationary phase can be connected to tubings, syringes, needles, valves or further containers.

The liquid phase for the purification process is selected from the group of organic solvents, water, aqueous solutions of salts, acids, bases or additives and mixtures thereof. In a preferred embodiment, the liquid phase is selected from the group comprising: pentane, hexane, heptane, octane, cyclopentane, cyclohexane, isooctane, toluene, p-xylole, chlorobenzene, benzene, diethylether, diisopropylether, tert-butyl methyl ether, nitromethane, chloroform, dichloromethane, 1,2-dichloroethane, triethylamine, pyridine, ammonia, acetone, tetrahydrofuran, ethyl acetate, methyl acetate, acetonitrile, isopropanol, ethanol, methanol, acetic acid, trifluoroacetic acid, water, saline solutions, buffers and mixtures thereof.

The liquid phase is passed through the container by means known to the persons skilled in the art. In a preferred embodiment, the liquid phase is passed through the container via a pump, a syringe, a syringe pump, a gas stream, vacuum or by combinations thereof.

Different kinds of detectors could be combined with the present process. Preferred detectors are: UV-detector, radioactivity detector, light scattering detector, conductometric detector, refractory index detector.

In a second aspect, the present invention relates to processes for the automated production of radiopharmaceuticals comprising the steps of:

radiolabeling of a precursor molecule and,
  purification of the radiolabeled tracer from excess of precursor and by-products using a container.
  Optionally, further chemical transformations can be part of the process.

The purification of the radiotracer comprises the step of liquid chromatography, wherein this liquid chromatography is a low- to medium-pressure liquid chromatography. In a preferred embodiment, the pressure of the liquid chromatography is between 1 and 20 bar, more preferable between 1 and 10 bar.

The radiolabeled compound contains at least one radioisotope that is selected in the group $^{99m}Tc$, $^{111}In$, $^{18}F$, $^{201}Tl$, $^{123}I$, $^{124}I$, $^{125}I$, $^{131}I$, $^{34}Cl$, $^{11}C$, $^{32}P$, $^{72}As$, $^{76}Br$, $^{89}Sr$, $^{153}Sm$, $^{186}Re$, $^{188}Re$, $^{212}Bi$, $^{213}Bi$, $^{89}Zr$, $^{86}Y$, $^{90}Y$, $^{67}Cu$, $^{64}Cu$, $^{192}Ir$, $^{165}Dy$, $^{177}Lu$, $^{117m}Sn$, $^{213}Bi$, $^{212}Bi$, $^{211}At$, $^{225}Ac$, $^{223}Ra$, $^{169}Yb$, $^{68}Ga$ and $^{67}Ga$.

In a preferred embodiment, the radiolabeled tracer is bearing a radioactive isotope for positron-emission-tomography.

In a more preferred embodiment, the radioisotope is selected from the group comprising $^{18}F$, $^{68}Ga$.

The container is a cartridge, column or any kind of cylinder.

The container is made from any kind of metal, alloy, plastic, glass, carbon or mixtures thereof.

In a preferred embodiment the material for the container is selected from the group of any kind of plastic, glass or mixture thereof, more preferably selected from USP class VI plastics, and even more preferably from medical-grade polyethylene or polypropylene.

The container is filled with a stationary phase.

The container can contain additional parts such as but not limited to: porous frits, connectors and adaptors.

In a preferred embodiment, the stationary phase is selected from the group comprising silica gel, modified silica gel, alumina, resins, polymers, copolymers or mixtures or layers thereof.

In a more preferred embodiment, the stationary phase is selected from the group comprising silica, alumina A, alumina B, alumina N, magnesium silicate, magnesium oxide, zirconium oxide, C30, C18, tC18, C8, C4, C2, tC2, amino propyl (NH2), cyano propyl (CN), diol, hydroxyapatite, cellulose, graphitized carbon and polystyrene/divinylbenzene polymers or copolymers thereof.

10 µg to 100 g of the stationary phase are filled into the container. In a preferred embodiment, 100 mg to 50 g of the stationary phase are filled into the container. In a more preferred embodiment 2 g to 20 g of the stationary phase are filled into the container.

One or more of the containers of same or different dimension filled with the same or different stationary phases can be used for the process.

The container filled with the stationary phase can be connected to tubings, syringes, needles, valves or further containers.

The liquid phase for the purification process is selected from the group of organic solvents, water, aqueous solutions of salts, acids, bases or additives and mixtures thereof. In a preferred embodiment, the liquid phase is selected from the group comprising: pentane, hexane, heptane, octane, cyclopentane, cyclohexane, isooctane, toluene, p-xylole, chlorobenzene, benzene, diethylether, diisopropylether, tert-butyl methyl ether, nitromethane, chloroform, dichloromethane, 1,2-dichloroethane, triethylamine, pyridine, ammonia, acetone, tetrahydrofuran, ethyl acetate, methyl acetate, acetonitrile, isopropanol, ethanol, methanol, acetic acid, trifluoroacetic acid, water, saline solutions, buffers and mixtures thereof.

The liquid phase is passed through the container by means known to the persons skilled in the art. In a preferred embodiment, the liquid phase is passed through the container via a pump, a syringe, a syringe pump, a gas stream, vacuum or by combinations thereof.

Different kinds of detectors could be combined with the present process. Preferred detectors are: UV-detector, radioactivity detector, light scattering detector, conductometric detector, refractory index detector.

The process is an automated procedure for manufacturing of the radiolabeled tracer.

In one embodiment, the purification process is a standalone automated procedure combined with an automated synthesis of the radiotracer.

In an other embodiment, the purification process is integrated into an automated synthesis of the radiotracer. In a preferred embodiment, a synthesizer is used for the production of the radiotracer and the purification process is established on the synthesizer. More preferably, the process of production and purification is performed without any manual operation.

In a preferred embodiment synthesis and purification of the radiotracer by "Medium pressure chromatography" are performed on a "Cassette type module" for the production of radiotracers know to the person skilled in the art, such as but not limited to: GE tracerlab MX (Coincidence FDG), GE Fastlab, IBA Synthera. Preferably, the container for "Medium pressure chromatography" is part of the disposable cassette (or kit).

In a third aspect, the present invention relates to disposable kits for processes for the production of radiopharmaceuticals comprising the steps of:

Radiolabeling of a precursor molecule and,

Purification of the radiolabeled tracer from excess of precursor and by-products using a container.

Optionally, further chemical transformations can be part of the process.

The kit comprises materials for the synthesis of the radiotracer and the container for purification, wherein the container is defined as described above.

The invention further relates to the following counts:
1. A method for production of radiotracers comprising a purification step using low- to medium-pressure liquid chromatography, wherein one or more than one container filled with a stationary phase is used.
2. A process according to count 1, wherein the radiotracer is a positron-emission radiotracer.
3. A process according to counts 1-2, wherein the stationary phase is selected from the group consisting of silica gel, modified silica gel, alumina, resins, polymers, gels or mixtures or layers thereof are used.
4. A process according to counts 1-3, wherein a container filled with a stationary phase selected from the group comprising silica, alumina A, alumina B, alumina N, magnesium silicate, magnesium oxide, zirconium oxide, C30, C18, tC18, C8, C4, C2, tC2, amino propyl (NH2), cyano propyl (CN), diol, hydroxyapatite, cellulose, graphitized carbon, polystyrene/divinylbenzene polymers, polystyrene/divinylbenzene copolymers or mixtures thereof is used.
5. A process according to counts 1-4 wherein the container is filled with 10 μg to 100 g of the stationary phase.
6. A process according to counts 1-5 wherein the container is filled with 2 g to 20 g of the stationary phase.
7. A process according to counts 1-6 wherein the solvent for the liquid chromatography is selected from the group consisting of organic solvents, water aqueous solutions of salts, acids or bases or additives and mixtures thereof.
8. A method according to counts 1-7 wherein the container is integrated into automated synthesis of a radiotracers.
9. A kit for the production of a radiotracer bearing a container for low-to medium-pressure liquid chromatography.
10. A kit according to count 9 for single use within the production of a radiotracer.

EXAMPLE 1

Synthesis and Purification of 4-[(E)-2-(4-{2-[2-(2-[F-18]fluoroethoxy)ethoxy]ethoxy}-phenyl)vinyl]-N-methylaniline

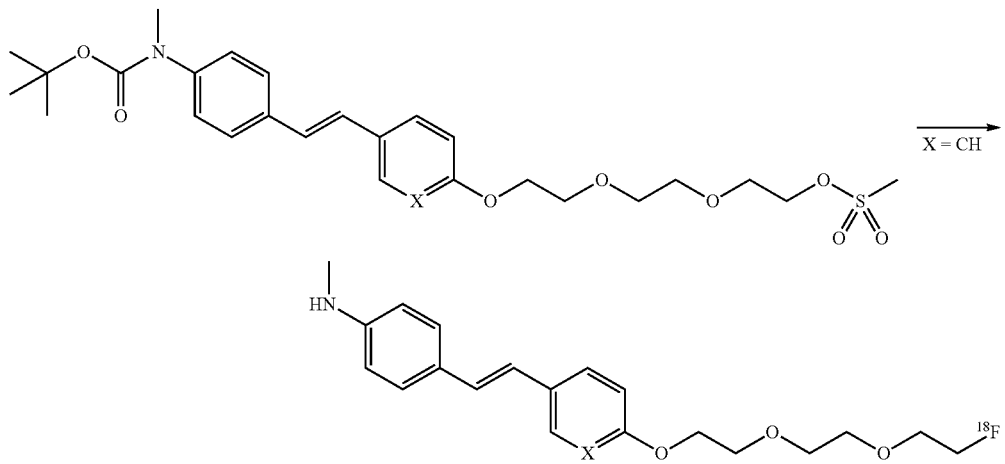

Figure 1:
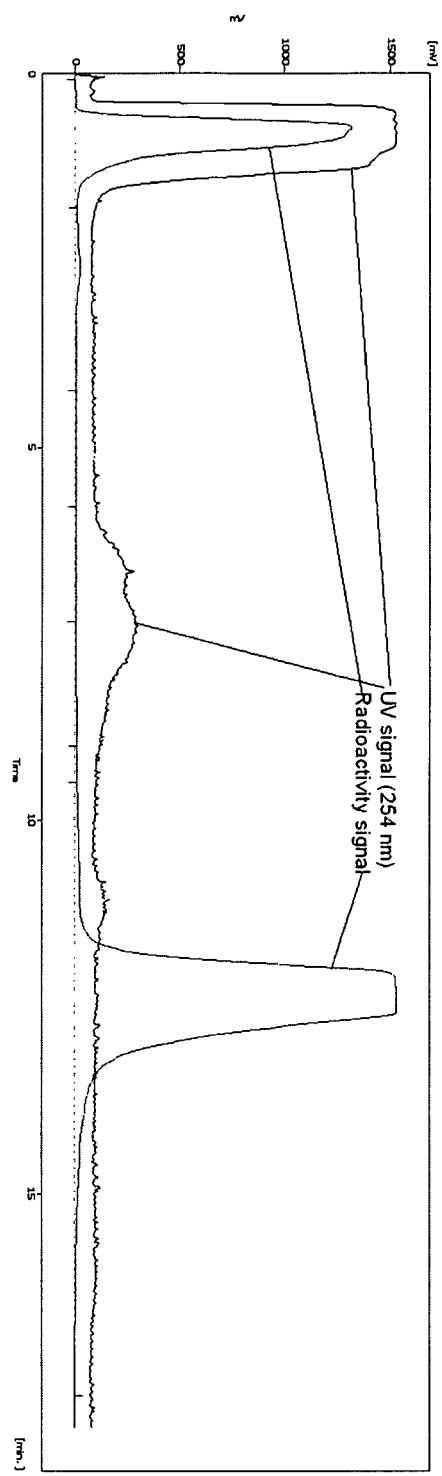
FIG. 1: Chromatogram of medium pressure chromatography of crude 4-[(E)-2-(4-{2-[2-(2-[F-18]fluoroethoxy)ethoxy]ethoxy}-phenyl)vinyl]-N-methylaniline.

[F-18]Fluoride (1.0 GBq) was trapped on a QMA cartridge (SepPak light, Waters). After elution with tetrabutylammonium hydroxide solution (300 μL 4% tetrabutylammonium hydroxide in water and 700 μL acetonitrile), the mixture was dried under gentle nitrogen stream at 120° C. Drying was repeated after addition of acetonitrile. 3.5 mg mesylate precursor were dissolved in 1.8 mL acetonitrile and added to the dried residue. The resulting mixture was heated at 110° C. for 10 min. 2 mL 1.5M HCl were added and the solution was heated at 110° C. for 5 min. 1.5 mL 2M NaOH were added and the solution was passed through a RediSep, Rf Gold HP C18 cartridge (5.5 g). A mixture of 40% ethanol and 60% 0.01M aqueous $Na_2HPO_4$ (pH 7.4) was passed through the cartridge with 10 mL/min using a preparative HPLC pump (Knauer smartline). After 10 min, a mixture of 50% ethanol and 50% 0.01M aqueous $Na_2HPO_4$ (pH 7.4) was passed through the cartridge with 10 mL/min. A fraction was collected from 12-13 min (FIG. 1).

Figure 2:
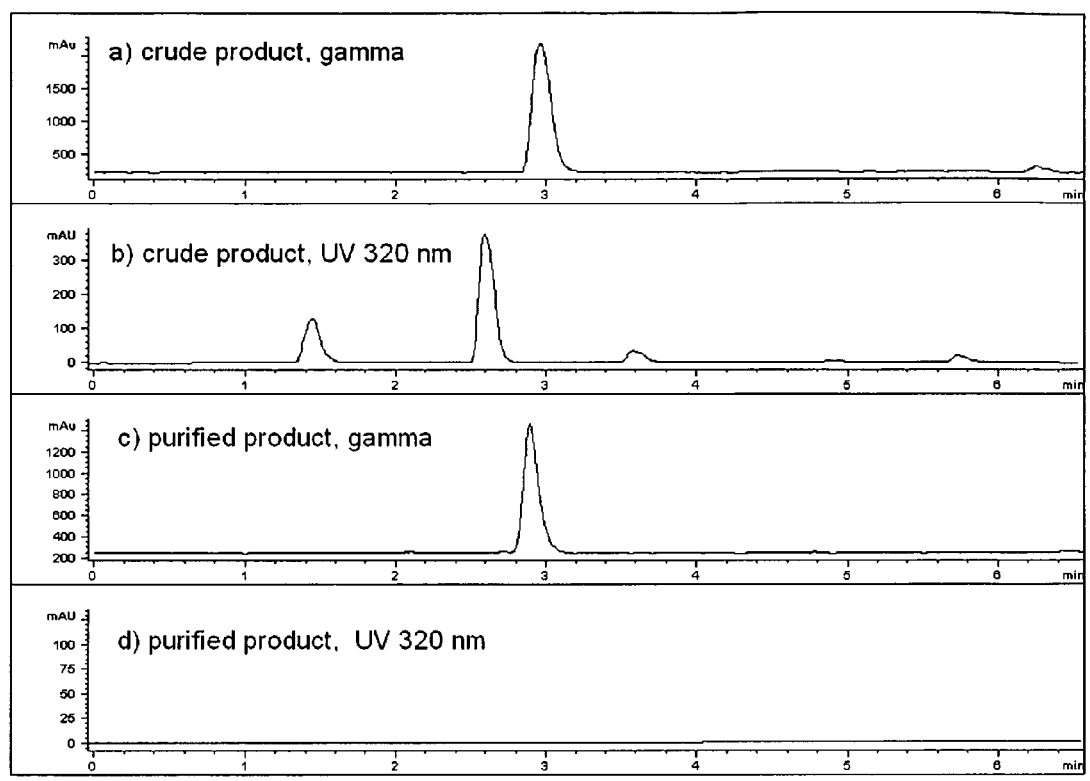
FIG. 2: Analytical HPLC chromatograms (Atlantis T3; 150*4.6 mm; 3 μm; Merck Waters; 40-90% MeCN in 5 mM $KH_2PO_4$ pH 2.2) of crude product mixture (a, b) and purified product (c, d) after "Medium pressure chromatography".

283 MBq (42% d.c.) 4-[(E)-2-(4-{2-[2-(2-[F-18]fluoroethoxy)ethoxy]ethoxy}-phenyl)vinyl]-N-methylaniline were obtained in 62 min overall synthesis time (FIG. 2).

Radioactive and non-radioactive impurities were successfully removed to provide the same quality of the tracer as after purification with semipreparative HPLC (e.g. Zorbax Bonus RP, Agilent; 55% MeCN in 0.1M ammonium formiate).

EXAMPLE 2

Figure 3:
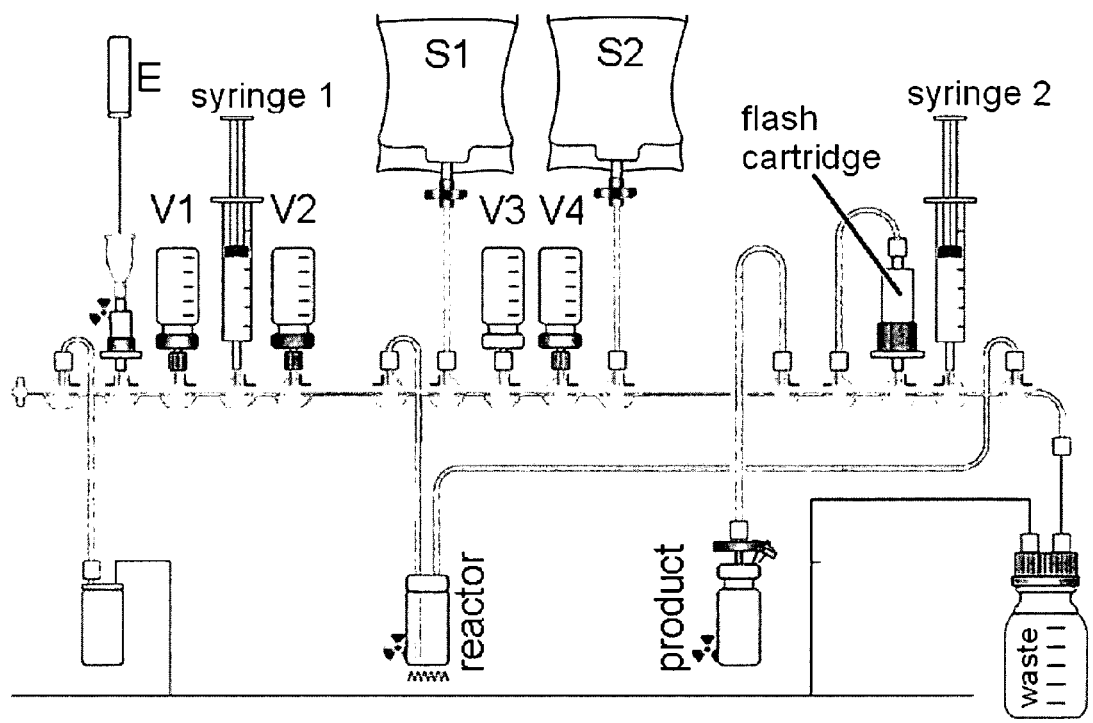
FIG. 3: Setup of tracerlab MX synthesis (picture was copied from Coincidence software and modified).

Automated Synthesis and Purification of 4-[(E)-2-(4-{2-[2-(2-[F-18]fluoroethoxy)ethoxy]-ethoxy}phenyl)vinyl]-N-methylaniline on Tracerlab MX Module Synthesis and purification of 4-[(E)-2-(4-{2-[2-(2-[F-18]fluoroethoxy)ethoxy]-ethoxy}phenyl)vinyl]-N-methylaniline were performed on a GE tracerlab MX module. A commercially available cassette for FDG synthesis was modified and assembled (FIG. 3):

The tC18 cartridge between manifold 2 and manifold 3 was replaced by a tube
The cartridges (tC18 and alumina) at manifold 3 were removed
Vial V1: 8 ml acetonitrile
Vial V2: 3.5 mg mesylate precursor in 1.5 mL acetonitrile
Vial V3: 1.5 mL 2M NaOH and 7 mL water
Vial V4: 30 mg sodium ascorbate and 2 mL 1.5M HCl
Vial E: potassium carbonat/kryptofix (in acetonitrile/water)
S1: 40% EOH, 60% 0.01 M aqueous $Na_2HPO_4$ (pH 7.4)—solvent 1
S2: 50% EOH, 50% 0.01 M aqueous $Na_2HPO_4$ (pH 7.4)—solvent 2
Flash cartridge: RediSep, Rf Gold HP C18 cartridge (5.5 g)

The synthesis sequence was started, involving the steps of:
1. Trapping of [F-18]fluoride on a QMA cartridge (SepPak light, Waters)
2. Elution of [F-18]fluoride using the mixture in E to the reactor
3. Evaporation of the solvent (repeated after addition of acetonitrile from V1)
4. Addition of precursor solution from V2 to the dried residue in the reactor
5. Heating at 110° C. for 10 min.
6. Transfer of acid in V4 into syringe 2
7. Transfer of acid from syringe 2 to syringe 1
8. Transfer of acid from syringe 1 to reactor
9. Heating at 110° C. for 5 min.
10. Transfer of NaOH in V3 into syringe 2
11. Transfer of NaOH from syringe 2 to syringe 1
12. Transfer of crude product from reactor to syringe 1
13. Trapping of crude product on flash cartridge
14. Washing of syringe 1 and manifolds with solvent 1
15. Flushing of flash cartridge by syringe 1 with solvent 1 (5 times 25 mL) into waste
16. Transfer of 25 mL solvent 2 to syringe 2
17. Transfer solvent 2 from syringe 2 to syringe 1

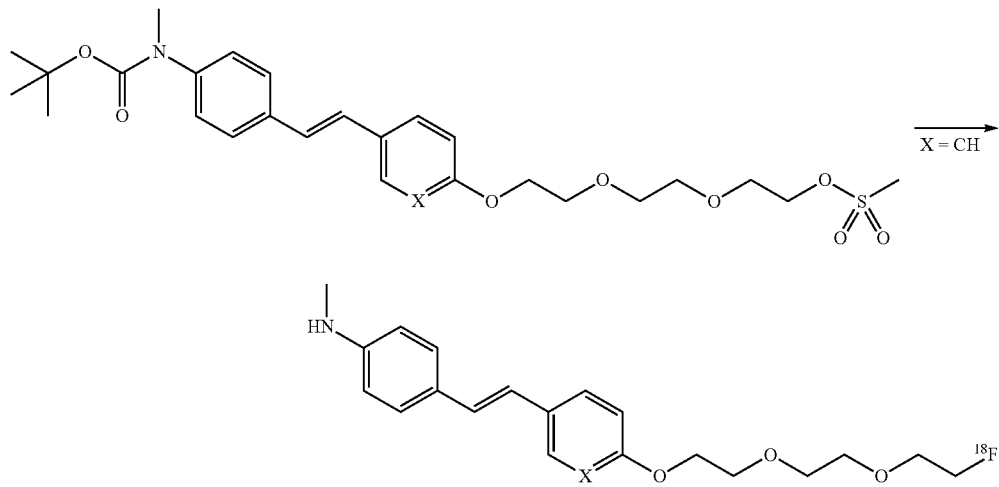

18. Flushing of flash cartridge with solvent 2 by syringe 1 into waste
19. Flushing of flash cartridge with 10 mL solvent 2 by syringe 1 into syringe 2
20. Passing of product fraction from syringe 2 into product vial.

Starting from 1.6 GBq [F-18]fluoride 380 MBq (36% d.c.) 4-[(E)-2-(4-{2-[2-(2-[F-18]fluoroethoxy)ethoxy]-ethoxy}phenyl)vinyl]-N-methylaniline were obtained in overall 65 min without any manual operation during synthesis and purification.

EXAMPLE 3

Synthesis and Purification of 4-[(E)-2-(6-{2-[2-(2-[F-18]fluoroethoxy)ethoxy]ethoxy}pyridin-3-yl)vinyl]-N-methylaniline

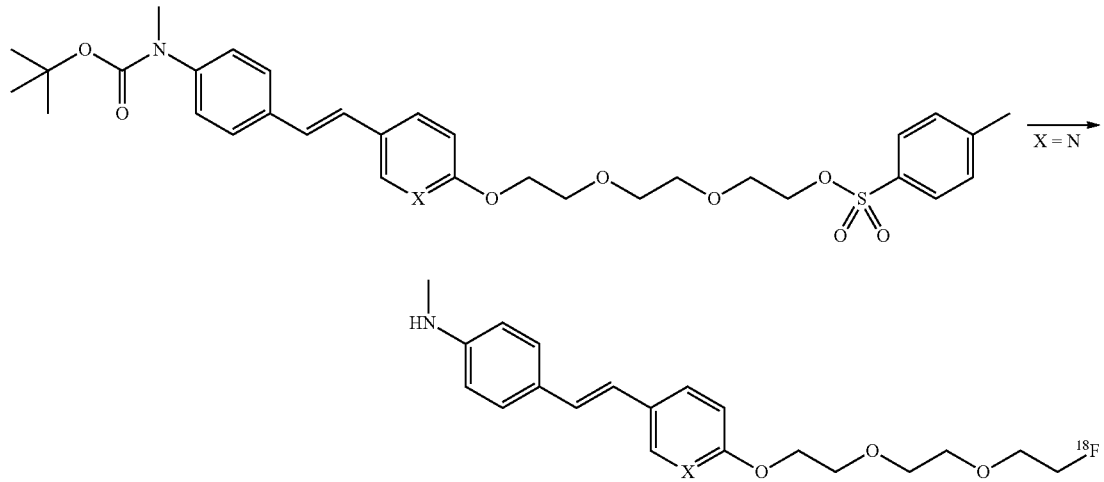

Figure 4:
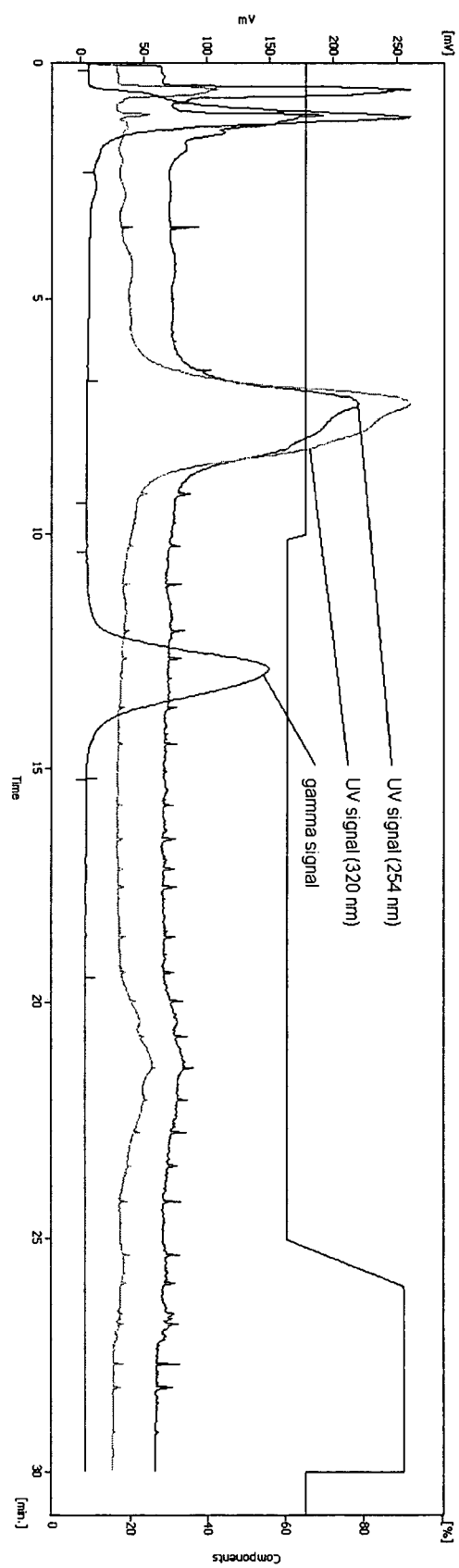
FIG. 4: Chromatogram of medium pressure chromatography of crude 4-[(E)-2-(6-{2-[2-(2-[F-18]fluoroethoxy)ethoxy]ethoxy}pyridin-3-yl)vinyl]-N-methylaniline.
Figure 5:
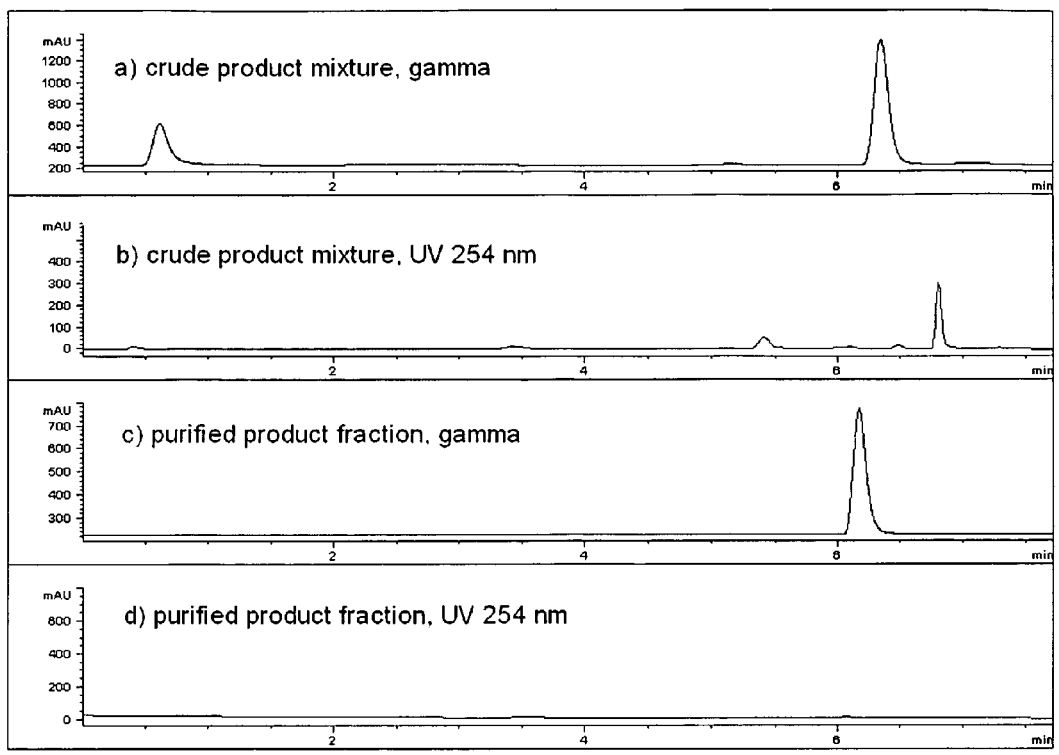
FIG. 5: Analytical HPLC chromatograms (Chromolith SpeedRod; Merck; 0-95% MeCN in 10 mM $Na_2HPO_4$ pH 7.4) of crude product mixture (a, b) and purified product (c, d) after "Medium pressure chromatography".

[F-18]Fluoride (1.24 GBq) was trapped on a QMA cartridge (SepPak light, Waters). After elution with potassium carbonate/kryptofix mixture (5 mg kryptofix, 1 mg potassium carbonate in acetonitrile/water), the mixture was dried under gentle nitrogen stream at 120° C. Drying was repeated after addition of acetonitrile (2×1 mL). 4 mg tosylate precursor were dissolved in 1 mL acetonitrile and added to the dried residue. The resulting mixture was heated at 110° C. for 10 min. After cooling to approximately 60° C., 500 µL 2M HCl were added and the solution was heated at 110° C. for 5 min. The mixture was allowed to cool to 60° C. 1 mL 1M NaOH and 2.5 mL were added and the solution was passed through a RediSep, Rf Gold HP C18 cartridge (5.5 g). A mixture of 35% ethanol and 65% 0.01M aqueous $Na_2HPO_4$ (pH 7.4) was passed through the cartridge 10 mL/min using a preparative HPLC pump (Knauer smartline). After 10 min, a mixture of 40% ethanol and 60% 0.01M aqueous $Na_2HPO_4$ (pH 7.4) was passed through the cartridge 10 mL/min. A fraction was collected from 12.6-13.6 min (FIG. 4). 337 MBq (44% d.c.) 4-[(E)-2-(6-{2-[2-(2-[F-18]fluoroethoxy)ethoxy]ethoxy}pyridin-3-yl)vinyl]-N-methylaniline were obtained in 75 min overall synthesis time (FIG. 5).

EXAMPLE 4

Automated Synthesis and Purification of (4-[F-18]fluorobenzyl)(triphenyl)phosphonium bromide on Eckert&Ziegler Modular Lab

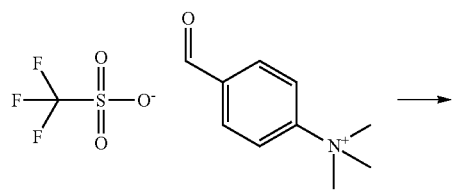

-continued

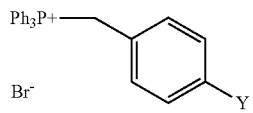

The synthesis and purification was performed on a Eckert&Ziegler modular lab. Starting from [F-18]Fluoride (4.67 GBq) (4-[F-18]fluorobenzyl)(triphenyl)phosphonium bromide was synthesized analogical to previous descriptions (Ravert, Journal Labelled Compounds and Radiopharmaceuticals, 2004, 469; WO2003065882; WO2006121035).

Figure 6:
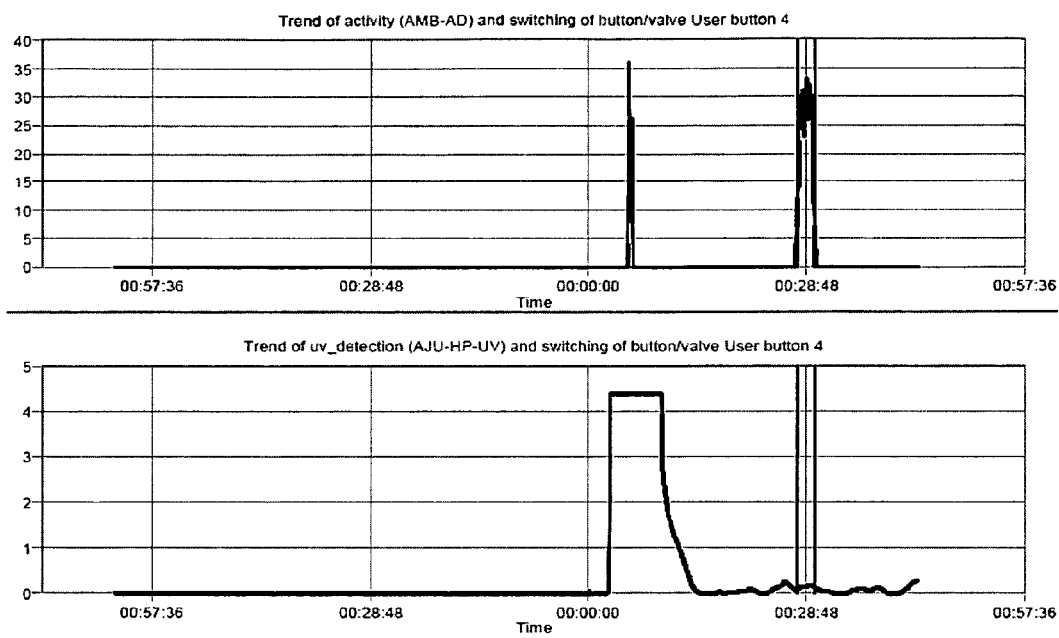
FIG. 6: Chromatogram of medium pressure chromatography on Eckert&Ziegler modular lab of crude 4-[F-18]fluorobenzyl)(triphenyl)phosphonium bromide, top: gamma, bottom: UV signal.
Figure 7:
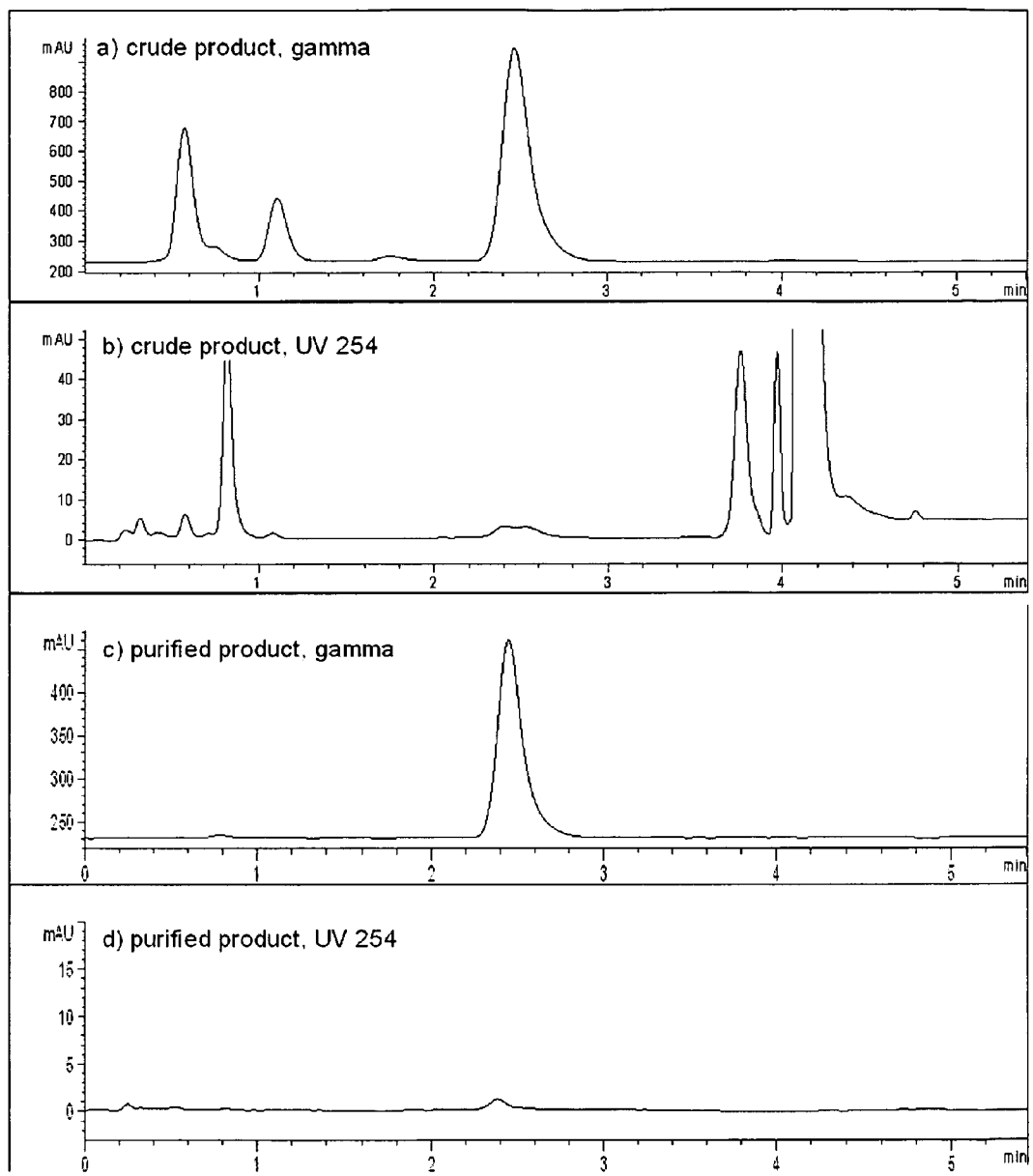
FIG. 7: Analytical HPLC chromatograms (Zorbax SB-C18; Agilent; 50% MeCN in 0.1M ammonium formiate) of crude product mixture (a, b) and purified product (c, d) after "Medium pressure chromatography".

The crude product mixture in 5 mL with acetonitrile was transferred onto a Biotage SNAP Cartridge (HP-Sil, 10 g, Biotage). The cartridge was washed with acetonitrile with 5 min/min. After 10 min, the cartridge was washed with 10% ethanol in acetonitrile (5 ml/min). The fraction from 27:14 min to 30:07 min was collected into a flask filled with 80 mL water (FIG. 6). The solution was passed through a C18 cartridge (SepPak plus, Waters). The cartridge was washed with 10 mL water and the product was eluted with 2 mL ethanol. 784 MBq (35% d.c.) 4-[F-18]fluorobenzyl)(triphenyl)phosphonium bromide were obtained in 118 min overall synthesis time (FIG. 7).

EXAMPLE 5

Synthesis and Purification of 4-[(E)-2-(4-{2-[2-(2-[F-18]fluoroethoxy)ethoxy]-ethoxy}phenyl)vinyl]-N-methylaniline on GE Tracerlab MX

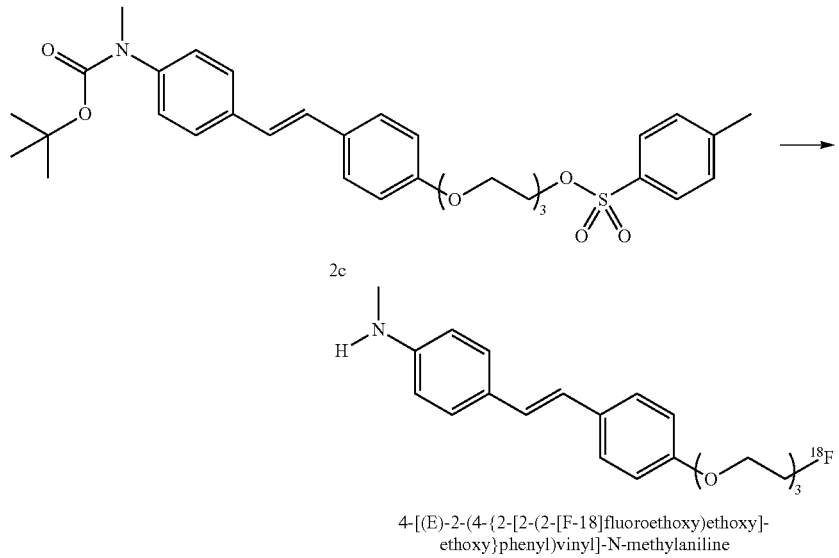

2c

4-[(E)-2-(4-{2-[2-(2-[F-18]fluoroethoxy)ethoxy]-ethoxy}phenyl)vinyl]-N-methylaniline For synthesis and purification of 4-[(E)-2-(4-{2-[2-(2-[F-18]fluoroethoxy)ethoxy]-ethoxy}phenyl)vinyl]-N-methylaniline on the Tracerlab MX, a Kit was assembled (Table 1).

TABLE 1

Composition of Kit for manufacturing of 4-[(E)-2-(4-{2-[2-(2-[F-18]fluoroethoxy)ethoxy]-ethoxy}phenyl)vinyl]-N-methylaniline on tracerlab MX

| | |
|---|---|
| Eluent vial | 22 mg kryptofix. 7 mg potassium carbonate in 300 μL water + 300 μL acetonitrile |
| Blue capped vial | 8 mL acetonitrile |
| Red capped vial | 8 mg precursor 2c |
| Green capped vial | 2 mL 1.5M HCl |
| 2 mL syringe | 1.5 mL 2M NaOH + 0.3 mL phosphate buffer |
| Solvent bag 1 | 40% EtOH in phosphate buffer (pH 7.4) |
| Solvent bag 2 | 50% EtOH in phosphate buffer (pH 7.4) |
| Anion exchange cartridge | QMA light, Waters (pre-conditioned) |
| Purification cartridge | Chromabond Flash RS 4 Nucleodur 100-30 C18ec, Macherey-Nagel (4 g stationary phase) |
| Product vial | 50 mL vial |
| Formulation basis 1 | 100 mg Ascorbic acid |
| Formulation basis 2 | 122 mg $Na_2HPO_4 \cdot H_2O$, 8.9 mL PEG 400, 26.1 mL water |

Figure 8:
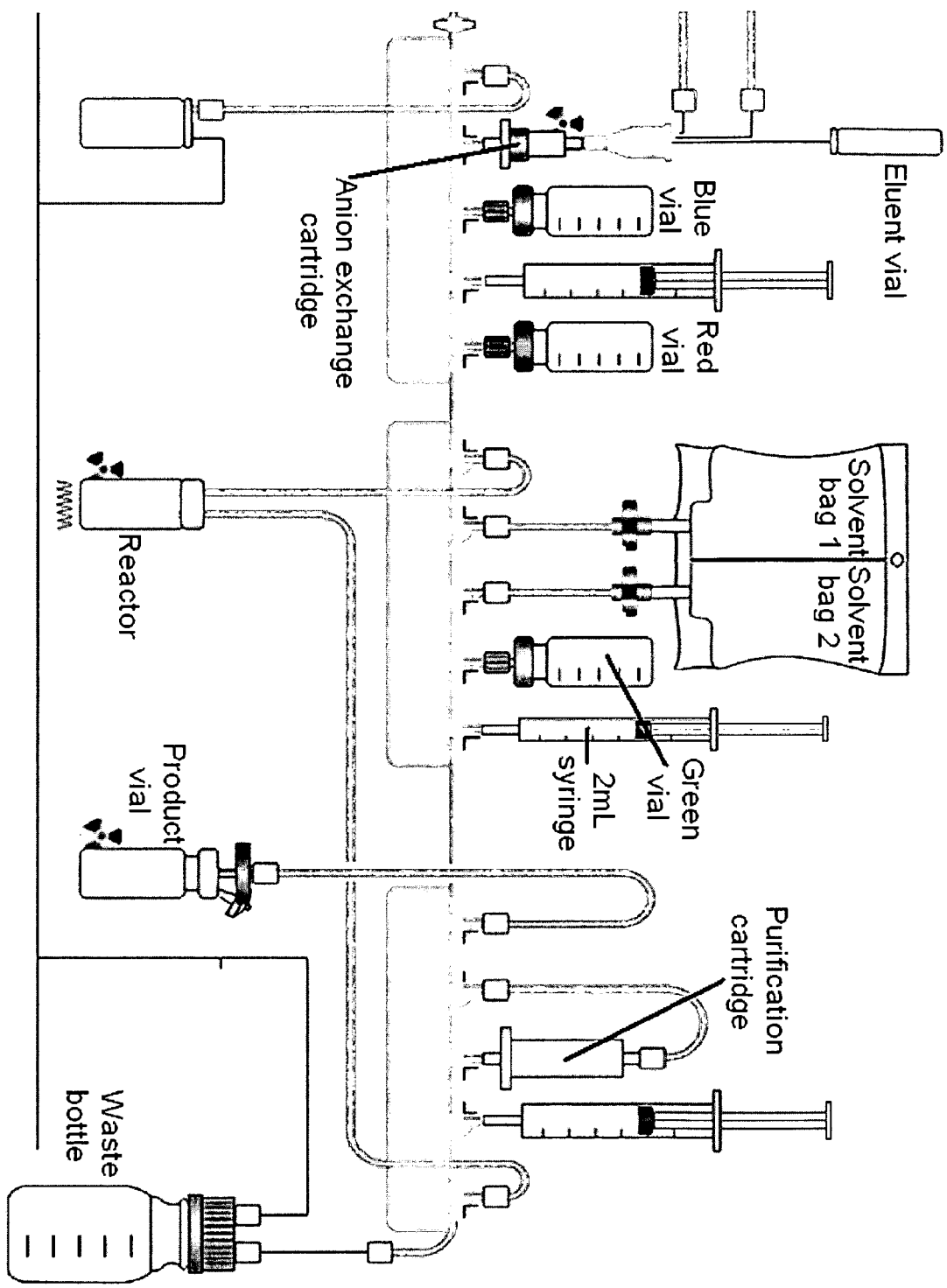
FIG. 8: Setup of Tracerlab MX for 4-[(E)-2-(4-{2-[2-(2-[F-18]fluoroethoxy)ethoxy]-ethoxy}phenyl)vinyl]-N-methylaniline synthesis (adopted from coincidence FDG software)

The setup of the cassette on the MX module is illustrated in FIG. 8.

Figure 9:
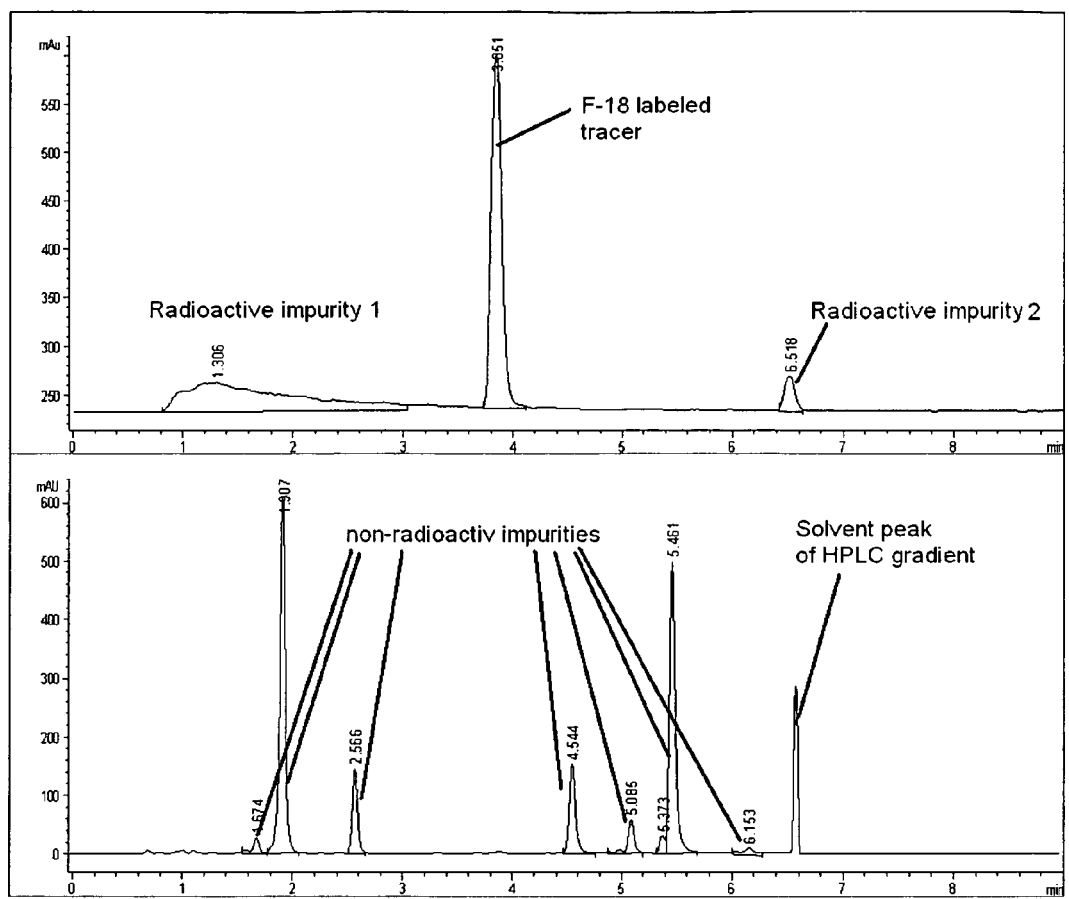
FIG. 9: Analytical HPLC of rude product of MX synthesis prior passing through "Purification cartridge" (sample was taken from reactor); top radioactivity; bottom: UV signal 320 nm
Figure 10:
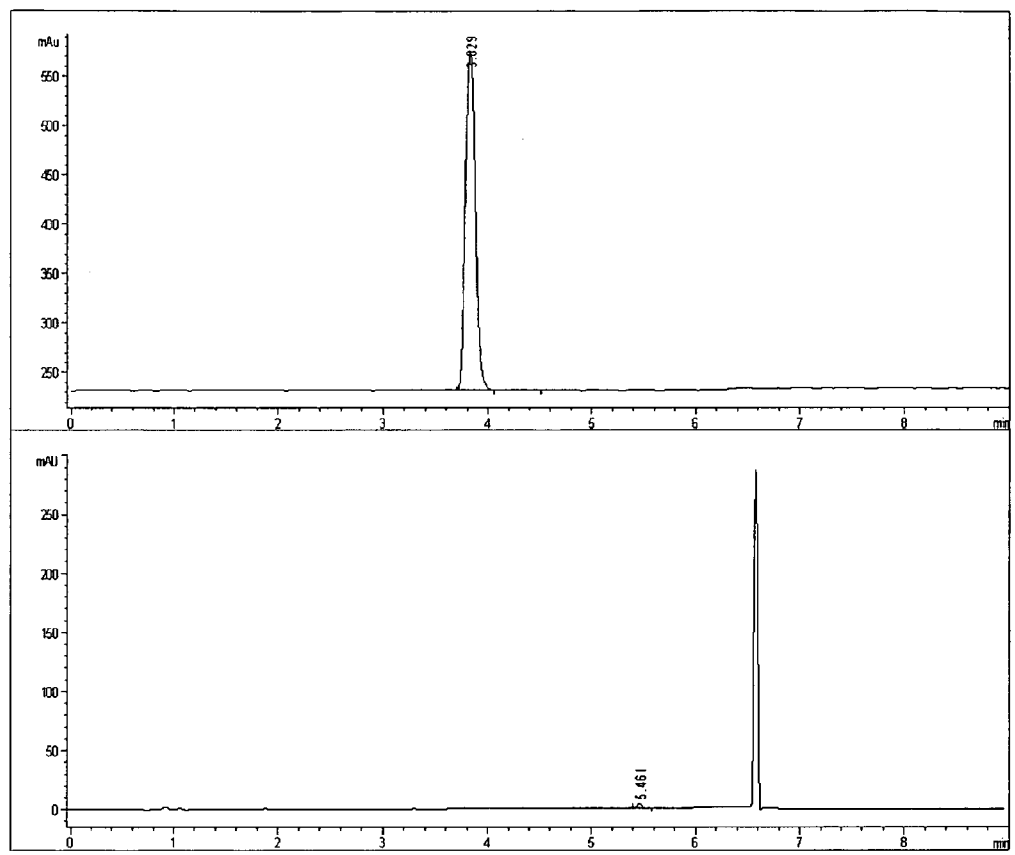
FIG. 10: Analytical HPLC of 4-[(E)-2-(4-{2-[2-(2-[F-18]fluoroethoxy)ethoxy]-ethoxy}phenyl)vinyl]-N-methylaniline after MX synthesis and cartridge based purification; top radioactivity; bottom: UV signal 320 nm

Precursor 2c was dissolved in the "red capped vial" during the synthesis sequence using approximately 1.8 mL acetonitrile from the "blue capped vial". Fluoride (2.4 GBq) was transferred to the MX module and trapped on the QMA cartridge. The activity was eluted into the reactor with potassium carbonate/kryptofix mixture from the "eluent vial". After azeotropic drying (heating, vacuum, nitrogen stream and addition of acetonitrile from the "blue capped vial"), the solution of 2c in acetonitrile was transferred from the "red capped vial" into the reactor. The resulting mixture was heated for 10 min at 120° C. HCl was transferred via the syringes from the "green capped vial" into the reactor. The mixture was heated for 5 min at 110° C. During deprotection, solvent mixture 1 from "Solvent bag 1" was flushed through the "Purification cartridge" by the left syringe. The crude product mixture was mixed with sodium hydroxid/buffer mixture from the "2 mL syringe" and diluted with the solvent 1 from "Solvent bag 1". The diluted crude product mixture was passed through "Purification cartridge". The remove non-radioactive by-products, solvent 1 from "Solvent bag 1" was filled into the left syringe and flushed through the "Purification cartridge" into the waste bottle. This procedure was repeated six times. Solvent 2 from "Solvent bag 2" was filled into the right syringe and transferred to the left syringe. Solvent 2 was flushed by the left syringe through the "Purification cartridge". The first fraction was allowed to go to the waste bottle, but a fraction of 7.5 mL was automatically collected into the right syringe. Finally, the product fraction was transferred to the product vial (that was pre-filled with Formulation basis 1 and Formulation basis 2). 770 MBq (32% not corrected for decay) 4-[(E)-2-(4-{2-[2-(2-[F-18]fluoroethoxy)ethoxy]-ethoxy}phenyl)vinyl]-N-methylaniline were obtained in 58 min overall manufacturing time. The cartridge based purification provided radiochemical and chemical pure product, similar to the purity obtained by semi-preparative HPLC (FIG. 9, FIG. 10).

The invention claimed is:

1. A method for purifying a radiotracer comprising subjecting the radiotracer to low- to medium-pressure liquid chromatography, wherein the chromatography is conducted using one or more than one disposable container filled with 2 g to 20 g of a stationary phase and wherein the radiotracer is 4-[(E)-2-(4-{2-[2-(2-[F-18]fluoroethoxy)ethoxy]ethoxy}-phenyl)vinyl]-N-methylaniline, or 4-[(E)-2-(6-{2-[2-(2-[F-18]fluoroethoxy)ethoxy]ethoxy}pyridin-3-yl)vinyl]-N-methylaniline, wherein the stationary phase is selected from the group consisting of: silica, alumina A, alumina B, alumina N, magnesium silicate, magnesium oxide, zirconium oxide, C30, C18, tC18, C8, C4, C2, tC2, amino propyl, cyano propyl, diol, hydroxyapatite, cellulose, graphitized carbon, polystyrene/divinylbenzene polymers, polystyrene/divinylbenzene copolymers and mixtures thereof, and wherein the low- to medium-pressure liquid chromatography is conducted at a pressure of 1 to 20 bar.

2. The method according to claim 1 wherein the liquid chromatography is conducted in a solvent selected from the group consisting of organic solvents, water aqueous solutions of salts, acids or bases or additives and mixtures thereof.

3. The method according to claim 1 wherein method further comprises synthesis of the radiotracer.

4. The method according to claim 3 wherein the radiotracer is synthesized and purified on a cassette type module.

5. The method according to claim 4 wherein the container for the low to medium-pressure chromatography is assembled on the cassette.

6. The method according to claim 3 where the radiotracer that is synthesized and purified is 4-[(E)-2-(4-{2-[2-(2-[F-18]fluoroethoxy)ethoxy]ethoxy}-phenyl)vinyl]-N-methylaniline, the method comprising the steps of:
   Nucleophilic radiofluorination of a precursor of the compound,
   Optionally, protection group transformation,
   Loading of the crude product on a container for low to medium pressure chromatography,
   Washing the container with a solvent mixture, suitable to elute by-products from the container, wherein the solvent is flushed through the container at 1 to 10 bar, and
   Eluting of purified 4-[(E)-2-(4-{2-[2-(2-[F-18]fluoroethoxy)ethoxy]ethoxy}-phenyl)vinyl]-N-methylaniline from the container with a second solvent mixture, suitable to elute 4-[(E)-2-(4-{2-[2-(2[F-18]fluoroethoxy)ethoxy]ethoxy}-phenyl)vinyl]-N-methylaniline from the container, wherein the solvent is flushed through the container at 1 to 10 bar.

7. The method of claim 3, wherein the synthesis and purification of the radiotracer is by an automated method.

8. The method of claim 1, wherein the low- to medium-pressure liquid chromatography is conducted at a pressure of 1 to 10 bar.

9. The method of claim 1, wherein the low- to medium-pressure liquid chromatography is conducted at a pressure of 1 to 5 bar.

* * * * *